United States Patent [19]

Carcasona et al.

[11] Patent Number: 5,391,775
[45] Date of Patent: Feb. 21, 1995

[54] PROCESS FOR PRODUCTION OF DIACETYLRHEIN

[75] Inventors: Alfons Carcasona, Köln; Wolf Grimminger, Bergisch Gladbach, both of Germany; Pentti Heitala, Helsinki, Finland; Klaus Witthohn; Helga Zaeske, both of Overath, Germany

[73] Assignee: Madaus AG, Cologne, Germany

[21] Appl. No.: 236,682

[22] Filed: Apr. 29, 1994

Related U.S. Application Data

[63] Continuation of Ser. No. 909,228, Jun. 24, 1992, abandoned.

[30] Foreign Application Priority Data

Jun. 25, 1991 [DE] Germany ................ 4120989

[51] Int. Cl.⁶ .......................... C07C 50/34
[52] U.S. Cl. ................................ 552/262
[58] Field of Search ............... 552/262; 514/510

[56] References Cited

U.S. PATENT DOCUMENTS 4,244,968 1/1981 Friedmann ............... 424/308

FOREIGN PATENT DOCUMENTS 243968 4/1987 European Pat. Off. .
2508798 1/1983 France .
3200131 1/1982 Germany .

OTHER PUBLICATIONS

V. K. Murty et al, Chemical Examination of Cassia Fistula, Tetrahedron, 1967, vol. 23, 515 to 518.
Drugs of the Future, vol. IV, No. 6, 1979.
U. R. Zope et al, A short synthesis of diacerhein, Chemistry and Industry, Communication to the Editor, p. 124, Feb. 15, 1988.
Merck Index, 10th ed., 1983, p. 1179.

Primary Examiner—Johann Richter
Assistant Examiner—Kimberly J. Kestler
Attorney, Agent, or Firm—Felfe & Lynch

[57] ABSTRACT

The present invention provides a process for obtaining diacetylrhein, wherein diacetylrhein containing aloe-emodin components is subjected to a liquid-liquid partitioning between a polar organic solvent which is only partly miscible with water and an aqueous phase of pH 6.5. to 7.5 and the diacetylrhein is recovered and optionally recrystallised.

The present invention is also concerned with diacetylrhein obtainable by this process and with pharmaceutical compositions containing it.

9 Claims, No Drawings

PROCESS FOR PRODUCTION OF DIACETYLRHEIN

This application is a continuation of application Ser. No. 07/909,228, filed Jun. 24, 1992, now abandoned.

The present invention is concerned with a process for obtaining diacetylrhein of pharmaceutically usable purity with a residual content of undesired aloe-emodin derivatives of, in all, less than 20 ppm, the diacetylrhein obtainable according to this process and a pharmaceutical composition which contains this compound.

Diacetylrhein of the formula:

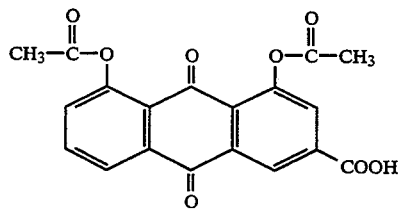

is a medicinally-active compound which possesses anti-arthritic, anti-inflammatory, antipyretic and analgesic activity. Therefore, diacetylrhein is used for the treatment of arthritic diseases (cf., for example DE-A-27 11 493 and US-A-4,244,968).

Diacetylrhein can be prepared, for example, by the acetylation of barbaloin and oxidation of the peracetylated barbaloin obtained with chromium trioxide. Furthermore, diacetylrhein Can be prepared by the acetylation of rhein which can be obtained, for example, from senna drug.

Diacetylrhein obtained according to these processes contains undesired accompanying aloe-emodin derivatives which result from an incomplete oxidation with chromium trioxide or are co-extracted in the case of the extraction of senna drug. These accompanying materials are present in relatively small amounts and can, therefore, only be separated with great difficulty by means of well-known purification procedures. Furthermore, in the case of the first of the above-mentioned processes, chromium residues are present which have to be removed in appropriate manner.

Therefore, it is an object of the present invention to provide a process for obtaining diacetylrhein which is simple to carry out and gives high yields and in which diacetylrhein is obtained of pharmaceutically usable purity with a residual content of undesired aloe-emodin derivatives of, in all, less than 20 ppm.

Thus, according to the present invention, there is provided a process for obtaining diacetylrhein, wherein diacetylrhein containing aloe-emodin derivatives (i.e. aloe-emodin and/or derivatives thereof) is subjected to a liquid-liquid partitioning between a polar organic solvent which is only partly miscible with water and an aqueous phase of pH 6.5 to 7.5 and the diacetylrhein is recovered and optionally recrystallised.

A diacetylrhein containing aloe-emodin can be used in the process according to the present invention. Important sources of diacetylrhein are the senna drug-containing sennosides, as well as the rhein-9-anthrone-8-glucoside obtainable from the sennosides.

Therefore, a preferred embodimental form of the present invention is a process for the preparation of diacetylrhein which is substantially free from aloe-amodin derivatives, wherein a) rhein-9-anthrone-8-glucoside containing aloe-emodin components is oxidised to the corresponding anthraquinone compounds, b) the glucose residue in the 8-position of the anthraquinone compounds is split off in an acid medium, c) the 1,8-dihydroxyanthraquinone compounds obtained are acetylated and d) a liquid-liquid partitioning of the product obtained is carried out between a polar organic solvent which is only partly miscible with water and an aqueous phase of pH 6.5 to 7.5 and the diacetylrhein is recovered and optionally recrystallised.

Another preferred embodiment of the present invention is a process for the preparation of diacetylrhein which is substantially free from aloe-emodin derivatives, wherein a) a sennoside mixture is subjected to a reduction to the corresponding enthrone compounds, b) the anthrone compounds obtained ere oxidised to the corresponding anthraquinone compounds, c) the glucose residue in the 8-position of the anthraquinone compounds is split off in an acid medium, d) the 1,8-dihydroxyanthraquinone compounds obtained are acetylated and e) a liquid-liquid partitioning of the product obtained is carried out between a polar organic solvent which is only partly miscible with water and an aqueous phase of pH 6.5 to 7.5 and the diacetylrhein is recovered and optionally recrystallised.

In the following, the individual steps of the process according to the .present invention are explained in more detail:

Reduction of the sennoside mixture to the corresponding an throne compounds

The sennoside mixture used as starting material can be obtained, for example, from senna drug. The senna drug consists of the dried leaves and fruits of the senna plant, for example of the Indian senna (Cassia angustifolia) and Egyptian senna (Cassia acutifolia). The senna drug contains dianthrone glucosides of rhein and aloe-emodin. The most important ones are sennosides A, B, Al, C, D and Dl. The sennosides correspond to the general formula:

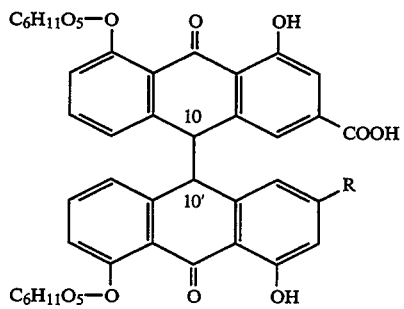

In the case of sennosides A, B and Al, R stands for COOH and in the case of sennosides C, D and Dl, R stands for $CH_2OH$. The sennosides A, B and Al and the sennosides C, D and Dl are stereoisomers and differ From one another by the configuration on carbon atoms 10 and 10'.

The obtaining of sennosides from senna drug is described, for example, in DE-A-32 00 131, reference to which is here made to the complete specification. According to this, the senna drug is first extracted with aqueous methanol. The concentrate remaining after complete removal of the methanol contains the sennosides in the form of alkali metal salts, preferably potassium salts. The concentrate is purified by liquid-liquid extraction with alcohols or ketones, for example butan-2-ol or butan-2-one, which are partly soluble in water (raffinate). The raffinate is acidified to a pH value of about 1.5 to 2.0 and the sennosides are crystallised by seeding out. The crude sennoside mixture obtained can be used as starting material for the process according to the present invention. If desired, the crude sennoside mixture can also be recrystallised.

Alternatively, the concentrate mixed with an alcohol which is only partly soluble in water, especially butan-2-ol, can be used as starting material for the process according to the present invention.

In the case of the extraction of the senna drug, the ratio of drug to extraction agent is preferably 1:4 to 1:15 and especially 1:4 to 1:10.

The extraction is preferably carried out in the presence of a buffer, for example trisodium citrate, glycine, sodium bicarbonate or saccharose.

According to the process of the present invention, these starting materials are reduced to give rhein-9-anthrone-8-glucoside (R=COOH) and aloe-emodin-9-anthrone-8-glucoside (R=CH$_2$OH) of the general formula:

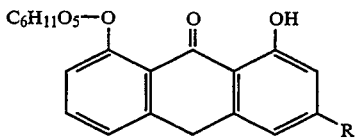

wherein R is COOH or CH$_2$OH.

Reducing agents with an appropriate reducing potential include stannous chloride, sulphur dioxide, alkali metal borohydrides and preferably alkali metal dithionites, especially sodium dithionite. The reducing agent is used in large excess. In general, a dithionite and especially sodium dithionite is used in a 1 to 4 fold amount by weight, referred to the content of sennosides in the starting material.

For carrying out the reduction, the starting material can be present in aqueous solution or suspension and the reducing agent added thereto in solid form or dissolved in water. It is preferred to work in a two-phase mixture by adding thereto a polar organic solvent which, at most, is only partly miscible with water, especially butan-2-ol.

The reduction is preferably carried out at a temperature of 40° to 60° C. and most preferably at 50° to 55° C. and at a pH of 7 to 9. The reduction is preferably carried out several times and most preferably 2 to 10 times.

The 9-anthrone-8-glucosides formed are precipitated out by the addition of an acid, for example of sulphuric acid, to a pH value of 4 to 4.5. The temperature should preferably be not more than 40° C. In the case of precipitating out of the anthrone glucosides and in the case of the isolation thereof, for example by filtration, it is preferable to work under an atmosphere of nitrogen in order to avoid an uncontrolled oxidation of these compounds.

Oxidation of the anthrone compounds to the anthraquinone compounds

The anthrone compounds obtained are now oxidised to the corresponding anthraquinone compounds of the general formula:

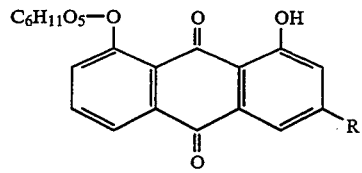

wherein R is COOH or CH$_2$OH. Oxidation agents appropriate for this purpose include, for example, oxygen, peroxide compounds, such as hydrogen peroxide, and manganese, chromium and iron compounds in high oxidation states. It is preferred to use a ferric salt and especially ferric sulphate. It is preferable to work at an elevated temperature but not greater than 60° C. The formation of undesired and undefinable oxidation products is avoided. After completion of the oxidation, the anthraquinone-8-glucosides are isolated in the usual manner.

Splitting off of the glucose residue

The glucose residue in the 8-position of the anthraquinone compounds is cleaned in an acidic solution. It is preferred to work at a temperature of about 85° to 95° C. The product obtained is isolated in the usual manner.

It is known to convert sennosides, after acidic hydrolysis, by reaction with ferric chloride directly into rhein (see for example DE-A-27 11 493). However, the yield is thereby only about 10% and, in addition, the rhein formed is difficult to separate.

In the case of the process according to the present invention, the reductive cleavage of the sennosides, the oxidation of the anthrone compounds formed to the corresponding anthraquinone compounds and the splitting off of the glucose residue in the 8-position of the anthraquinone compounds are, in each case, carried out in separate steps. Surprisingly, in this way, rhein is obtained in a yield of 89%. Furthermore, it is possible to carry out the oxidation at modest temperatures so that the formation of undesired and undefinable oxidation products is avoided. Furthermore, when carrying out the reaction, the iron salt used can be recovered and quantified and, after reoxidising, can be used again. The separation of oxidation step and hydrolysis step permits, on the basis of the greater water solubility of the anthrone glucosides in comparison with the aglycones in question, the carrying out of the oxidation at ambient temperature or at a temperature below 60° C. The otherwise usual formation of undefined by-products is avoided.

Acetylation of the 1,8-dihydroxyanthraquinone compound

The acetylation of the 1,8-dihydroxyanthraquinone compounds obtained takes place in the usual manner. For example, acetylation can be carried out with acetic anhydride in the presence of sodium acetate in the manner described in Arch. Pharm., 241, 607/1903. However, the acetylation can also take place by means of other methods known to the expert, for example by reaction with acetyl chloride or the like.

Liquid-liquid partitioning

A liquid-liquid partitioning of the product obtained is carried out in a polar organic solvent which, at most, is only partly miscible with water and an aqueous phase of pH 6.5 to 7.5. Appropriate polar organic solvents include $C_4$–$C_5$-alkanols and $C_1$–$C_3$-dialkyl ketones, for example butan-1-ol, butan-2-ol, isobutanol and butan-2-one, the latter being preferred.

The volume ratio of heavier to lighter phase is, in general, in the range of from 1:2 to.2:1. The lighter phase is a solution of the diacetylanthraquinone compounds in the polar organic solvent. As heavier phase, there is used an aqueous phase of pH 6.5 to 7.5 which is preferably adjusted with a buffer and especially with an acetate buffer.

The liquid-liquid extraction is preferably carried out in countercurrent, the diacetylrhein thereby being introduced into the organic phase in a concentration of about 0.01M.

After the partitioning, the desired diacetylrhein is present in the heavier phase. It is precipitated-out by acidification to a pH value of about 5.2 and then recovered in the usual manner and the diacetylrhein is recrystallised as an alkali metal salt and preferably as potassium salt, the salt then being converted into the insoluble free acid. Alternatively, direct recrystallisation can be performed from ethyl lactate.

The diacetylrhein obtained in this manner is substantially free from aloe-emodin and derivatives thereof. The content of these impurities thereby still amounts to about 50 ppm (determined by the analysis process described in the following Examples). The content of these impurities can be further reduced when the diacetylrhein obtained is recrystallised in the following manner. The diacetylrhein is converted into an alkali metal salt by treatment with an appropriate base, an appropriate base being, for example, an alkali metal acetate and preferably potassium acetate. It is preferable to use equimolar amounts of base and an aqueous $C_1$–$C_3$-alcohol, for example 80 to 90% ethanol, as reaction medium. The alkali metal salt of diacetylrhein is allowed to crystallise out in the cold, then taken up in an aqueous $C_1$–$C_3$-alcohol and precipitated out by the addition of an acid to a pH value of about 3. The diacetylrhein precipitated out is then isolated in the usual manner and worked up. As a variant a direct recrystallisation can be carried out from ethyl lactate.

The product thus obtained contains less than 20 ppm of the above-mentioned impurities. Furthermore, the product is present in the form of needle-shaped crystals which are especially appropriate for galenical formulation.

The product can be dried in the usual manner It is preferable first to carry out the drying in a vacuum at a relatively low temperature, for example of not more than 40° C., until the water content of the product has decreased to about 3% or less. Subsequently, the temperature can be increased to 70° to 110° C.

The present invention is also concerned with the substantially pure diacetylrhein obtainable according to the present invention, as well as with pharmaceutical compositions which contain this compound. The fields of use, the dosage to be administered and appropriate forms of dosaging are known from and described, for example, in U.S. Pat. No. 4,244,968, U.S. Pat. No. 4,346,103, U.S. Pat. No. 4,950,687 and DE-A-27 11 493, as well as in Drugs Exptl. Clin. Res., 6 (1), 53–64/1980.

The following Examples are given for the purpose of illustrating the present invention.

EXAMPLE 1

Obtaining the sennoside mixture used as starting material

In each case, 40 kg of senna drug (sennoside content about 1,5%) are introduced into two percolators, connected in series, with a volume of 250 litres and covered with a perforated steel plate. As solvent for the extraction, there is used 70% methanol which is passed to the drug in the first percolator. The solution formed in the first percolator is passed to the drug which is present in the second percolator. The solvent is thereby allowed to flow freely through the first percolator.

For the extraction of 40 kg of senna drug, a total of 160 litres of solvent is used. After this volume of 70% methanol has been passed through the two percolators and the corresponding amount of percolate has been collected, the emptying pipe of the percolator is coupled with a post-percolate container and an additional 60 litres of 70% methanol are passed through the percolators. Thereafter, the remaining free solvent from the first percolator is passed into the upper part of the second percolator and the post-percolate is collected until it amounts to 120 litres. The first percolator is then emptied again filled with 40 kg of senna drug and the post-percolate is pumped on to the drug, the 120 litres of post-percolate is sufficient to cover the drug in the percolator.

Subsequently, the temperature of the solution is adjusted to +30° C.

This percolator is connected with the one previously extracted, and the extraction is carried out as described above.

For each 40 kg of drug, 150 litres of percolate are collected from which the methanol is removed in a vacuum rotary evaporator which is equipped with a packed column about 30 litres of bottom product (concentrate) obtained which is extracted in a mixer-settler apparatus with 10 stages using 40 litres of butan-2-ol which is saturated with water. There are obtained about 38 to 40 litres of aqueous raffinate and about 30 to 32 litres of butan-2-ol extract.

The aqueous raffinate is acidified, while stirring, with 93% sulphuric acid over the course of 20 hours, use thereby being made of 1.6% by volume, referred to the volume of liquid to be acidified. The acidified solution then has a pH value of 1.5 to 2.0. It is stirred for a further 6 days, the precipitate is then allowed to settle out overnight, filtered off, washed with water until the wash water is colourless, washed with methanol and dried in a current of air at ambient temperature. The yield per 40 kg of raw material is 760 to 790 g (dry substance) of crude sennosides with a sennoside content of 90 to 94%. Thus, the yield accounts for about 70% of the amount of sennoside present in the raw material.

Step a)

Reduction of the sennosides to rhein-9-anthrone-8glucoside 9.0 kg of sodium dithionite are dissolved in 100 litres of demineralised water. The crude sennosides obtained, containing about 3.0 kg of sennosides A, Al and B, are metered, while stirring, into this solution. The homogeneous solution is stirred for 2 hours at 55° to 58° C. and then cooled to 50° to 55° C. Precipitation is then carried out with 96 to 98% by weight sulphuric acid at pH 4.2. The resulting suspension is stirred for a further 1.5 hours at a maximum temperature of 25° C. and then filtered under an atmosphere of nitrogen. The reside is washed with 50 litres of demineralised water which has been adjusted with sulphuric acid to pH 2. Subsequently, it is covered with 10 litres of ferric sulphate solution (preparation see step b).

Step b)

Oxidation to rhein-8-glucoside

The product from the preceding step is suspended in a solution of 184 litres of demineralised water and 75.7 kg of ferric Sulphate hydrate (22% $Fe^{3+}$). The suspension is heated to 55° to 62° C. and oxidised for 14 hours with the use of a rapidly running disperser. When the oxidation is complete, the rhein-8-glucoside is filtered off and washed with 50 litres of demineralised water which has been adjusted with sulphuric acid to pH 2.

Step c)

Hydrolysis to rhein

The moist filter residue from step b) is suspended in 200 kg of 20% by weight sulphuric acid and stirred for 8 hours at 88° to 92° C. The rhein formed is filtered off and, for storage, can be dried an 1 mbar vacuum for 48 hours at 40° C. or can be used immediately in a moist state for the acetylation in step d).

The total yield for steps a) to c) is 89%, referred to the sennosides A, A1 and B used in step a).

Step d)

Acetylation to give diacetylrhein 6.5 kg of rhein from step c) are suspended in 100 litres of acetic anhydride for 10 minutes, mixed with 2 kg of potassium acetate, heated to 95° C. while stirring, mixed with 0.65 kg of activated carbon and stirred for 30 minutes at 90° to 95° C. The activated carbon is filtered from the hot solution and the filtrate is mixed at 90° C. with 2.1 kg of 96 to 98% by weight of sulphuric acid. Subsequently, while stirring, it is cooled as quickly as possible to 20° C. and the resulting suspension is filtered. The residue is washed free of sulphate with demineralised water. The yield is 83%.

Step e)

Removal of free and acetylated aloe-emodin

The portion of aloe-emodin is removed by countercurrent extraction on a pulsed extraction column with at least 15 theoretical plates. The volume ratio of heavier to lighter phase is 1:1. As heavy phase, there is used a 0.1 molar aqueous potassium acetate solution saturated with butan-2-one. In the lighter phase, which consists of water-saturated butan-2-one, the diacetylrhein to be purified is dissolved 0.01 molar. The diacetylrhein is precipitated from the heavy phase running off with the use of 10% by weight sulphuric acid at pH 5.2. The precipitate is filtered off and washed free of sulphate with demineralised water. Yield 88%, referred to the crude diacetylrhein used from step d).

Step f)

Recrystallization, drying and grinding

Variant A

With rapid stirring, 7.5 kg of diacetylrhein from step e) (referred to the dry substance) are suspended in 250 litres of 90% by volume ethanol. The suspension is heated to 70° C. and then mixed with 3.75 kg of potassium acetate. Upon cooling to 0° to 2° C., the pure potassium salt of diacetylrhein crystallises out from the clear solution which has, in the meantime, formed. The potassium salt is filtered off and dissolved in 800 litres of 48% by volume ethanol at 20° to 30° C. The clear solution is adjusted with 10% by weight sulphuric acid to pH 3.0. The diacetylrhein which crystallises out is filtered off and washed free of sulphate with demineralised water.

Variant B 7.5 kg diacetylrhein are suspended in 275 litres ethyl lactate, brought into solution by heating, filtered and crystallises while stirring at 20° to 25° C. The crystallised diacetylrhein is filtered off and washed with demineralised water.

The product is first dried in a vacuum at 1 mbar and 40° C. within the course of 24 hours. When the residual water content has decreased to below 3%, the material is coarsely comminuted and further dried at 1 mbar vacuum and 70° C. for 24 hours. Subsequently, it is ground to a sieving size of 0.5 mm and again dried an 1 mbar vacuum and 70° C. for the removal of solvent residues. The yield from step f) is 95%.

EXAMPLE 2

The process described in Example 1 is repeated with, however, the following modifications:

In the case of the extraction of the senna drug, there is used trisodium citrate in that 2.85 kg of trisodium citrate are added to 40 kg amounts of the drug before addition of the solvent. As solvent, there is thereby used 70% methanol heated to 60° C. After removal of the methanol to a volume of 11.4 litres, the concentrate is mixed with about 2 litres of butan-2-ol.

The reduction of the senna fruit concentrate/ butan-2-ol mixture is then carried out in 7 steps under nitrogen as protective gas. After reduction step I, there follows a precipitation of the crude rhein-9-anthrone-8-glucoside. The reduction steps II to VII serve for the partial removal of aloe-emodin derivatives. These steps are carried out without precipitations. The final precipitation of the purified rhein-9-anthrone-8-glucoside takes place after the last reduction step.

Reduction Step I 100 litres of senna fruit concentrate/butan-2-ol mixture, containing about 4 kg of sennosides, are placed in a stirrer container and covered with nitrogen. While stirring, 6 litres of .20% by weight aqueous sodium hydroxide solution and thereafter 350 litres of water-saturated butan-2-ol (for example from step II by countercurrent) are successively added thereto, followed by stirring for 15 minutes. The batch is heated to 42°–50° C. mixed with 7 kg sodium dithionite and thereafter further stirred for 45 minutes. The pH value is maintained at 7.5 to 8 with 20% by weight aqueous sodium hydroxide solution. The reduction potential (against an Ag/AgCl electrode) is, if necessary, maintained at value below −630 mV by the addition of sodium dithionite. After cooling to 30° to 35° C., precipitation is carried out with 10% by weight sulphuric acid to pH<4 within a period of 1.5 hours. The resultant suspension is stirred at <25° C. for about 10 hours at a slow stirring speed. The resultant precipitate is filtered off. The precipitate is suspended in 60 litres of 15 % by weight butan-2-ol, stirred for 30 minutes at 50° to 60° C. and subsequently filtered. The residue is washed with 100 litres of demineralised water. The crude yield of rhein-9-anthrone-8-glucoside is more than 82%, referred to the sennoside used.

Reduction Step II 3.3 kg of crude rhein-9-anthrone glucoside from step I are suspended in a mixture of 42 litres of demineralised water and 7.4 litres of butan-2-ol. The suspension is brought into solution with 2 litres of 20% by weight aqueous sodium hydroxide solution and 9.9 kg trisodium citrate and thereafter mixed with 3.3 kg sodium dithionite and 350 litres of water-saturated butan-2-ol (for example by countercurrent from step III). The batch is heated to 42° to 45° C. The pH value is maintained at 8.5 to 9 with 20% by weight aqueous sodium hydroxide solution. The reduction potential (against an Ag/AgCl electrode) is, if necessary, maintained at a value below −750 mV by the addition of sodium thionite.

After standing for 30 minutes, .the upper phase is removed and the lower phase is further worked up in step III.

Reduction step III

With the lower phase from step II, the reduction described in step II is repeated with the addition of the following chemicals:
1.65 kg sodium dithionite
0.8 litres 20% by weight aqueous sodium hydroxide Solution
350 litres water-saturated butan-2-ol (e.g. by countercurrent from step. IV )

Reduction Steps IV–VII

With the lower phase from each of the preceding steps, the reduction/extraction process described in step II is repeated with the addition of the following chemicals:
0.825 kg sodium dithionite
0.4 litres 20% by weight aqueous sodium hydroxide Solution
350 litres water-saturated butan-2-ol (e.g. by countercurrent from the following steps)

The lower phase separated in step VII is cooled to 30° to 35° C. and the rhein-9-anthrone-8-glucoside precipitated out as described in step I. The resultant precipitate is filtered off and washed with 200 litres of demineralised water. Subsequently, it is covered with 10 litres of ferric sulphate solution (preparation see step B, Example 1).

The rhein-9-anthrone-8-glucoside is then converted into diacetylrhein as described in Example 1.

Pharmacological investigations

The effectiveness of diacetylrhein was determined in chronic inflammation models after oral administration. The following experimental models were used: cotton pellet granuloma in rats and arthrosis in rabbits induced by the intraarticular administration of vitamin A.

a) Cotton pellet granuloma in rats

Young sexually mature rats (n=10) were given 25, 50 or 100 mg diacetylrhein/kg or 5 mg indomethacin/kg or 100 mg acetylsalicylic acid/kg daily for 5 days. A control group only treated with water was also used. Implantation of the pellets took place on the first day of treatment. Fresh and dry weights of the granuloma prepared at the end of the experiment showed a significant and clearly dosage-dependent reduction in comparison with the control group. The action of 100 mg diacetylrhein/kg thereby corresponded to about the action of 5 mg indomethacin or of 100 mg acetylsalicylic acid. The weights of the thymus and adrenals did not change during the treatment.

b) Vitamin A arthrosis

An arthrosis-like joint change was initiated in two groups each of 10 rabbits (white New Zealanders) by means of three intraarticular injections of 30,000 IU of Vitamin A over the course of 9 days. 56 days later, 10 animals were treated with 3 mg of diacetylrhein/kg/day for 8 weeks. In comparison with the control group, the macroscopically and microscopically recognisable joint changes in the treatment group were significantly reduced.

Furthermore, the curative action of diacetylrhein was compared with that of acetylsalicylic acid on each of 7 rabbits which, after 6 days pre-treatment with three times 10,000 IU Vitamin A and a 26 day treatment-free interval for 8 weeks, received either 5 mg of diacetylrhein/kg/day (experimental group) or 15 mg of acetylsalicylic acid/kg/day (positive control group) or remained untreated (negative control group). In all three groups, 24 days after the last vitamin A injection, comparable disturbances of movement occurred in the form of dragging of the rear legs. In the negative control group, during the following 8 weeks, the clinical signs of a manifest arthrosis increased. In the experimental group and the positive control group, these symptoms improved significantly during the 8 weeks of treatment.

Gastric mucosa changes

Whereas a single administration of 400 mg of diacetylrhein/kg or of the solvent did not give rise to any erosions of the gastric mucosa in the rat, after the administration of ibuprofen (200 mg/kg) or of indomethacin (20 mg/kg), there were found distinct mucosal damages in the form of punctiform (1 mm diameter) to large (3 mm diameter) erosions. The twice daily administration of 100 mg diacetylrhein/kg over the course of 3 days also did not initiate any mucosal damage, whereas the corresponding use of 10 mg indomethacin/kg certainly did, the erosions thereby having a diameter of 1 to 3 mm.

Toxicology

The acute toxicity $LD_{50}$ was, depending upon the species investigated (rat, mouse, cat), after the oral administration, 1.9 to 7.9 g/kg. The rat thereby proved to be the least sensitive. After parenteral administration (i.v. or i.p.), the $LD_{50}$ values in the case of these species was from 119 to 339 mg/kg.

Clinical investigations

1. The action of diacetylrhein was investigated in coxarthrosis and gonarthrosis in 95 (49/46) patients in a double-blind study against naproxen and subsequent placebo after-treatment. The dosage administered was 50 mg of diacetylrhein twice daily or 750 mg of naproxen daily. The period of treatment was 60 days after a 7 day wash-out phase. The subsequent placebo treatment extended over 60 days.

Test parameters were the pain and movement symptoms according to a score scale, functional limitation and compatibility.

In both treatment groups (diacetylrhein/naproxen), with regard to all test parameters a statistically significant rate of improvement ($P<0.01$ and $P<0.05$, respectively ) was measured in comparison with the initial values. After discontinuation of the treatment and subsequent administration of placebo, there was shown, however, on days 90 and 120, with regard to the parameters of spontaneous pain and active and passive movement pain, a statistically significant superiority ($P<0.01$) in comparison with the naproxen/ placebo collective. On the 5% level, this difference was also verified for the variable night pain and pressure pain 30 days after discontinuation of diacetylrhein.

2. In an open running study with control, the action of diacetylrhein against osteoarthrosis of the spine and of the knee in 70 patients (35/35) was investigated. The dosage administered was 100 mg of diacetylrhein per day. The period of treatment was 60 days and the period of observation was 75 days. The test parameters were pain and movement limitation. The parameters were evaluated according to a score system.

The control group comprised 35 patients in the case of which exclusively physiotherapeutic measures were carried out. Physiotherapy was also carried out in the diacetylrhein treatment group.

With regard to all parameters, the evaluation the results showed a statistically significant superiority of the treatment group with regard to the control group. Also after discontinuation of the treatment, a continuing therapeutic effect (hang-over effect) could be ascertained for the diacetylrhein group.

3. The action of diacetylrhein in the case of localised arthrosis in 20 patients was investigated in a single blind crossover study against naproxen. The patients were divided up into two groups: in the first group, initially 50 mg of diacetylrhein was administered twice daily for 20 days. Subsequently, there followed a three day wash-out phase and a further treatment with 250 mg of naproxen twice daily for a further 20 days. In the second group, the reverse sequence was used. The period of treatment was, in all, 43 days. The test parameters of pain, compression pain, passive movement pain, functional limitation and Swelling were determined according to a score system.

The evaluation of the results showed a superiority of the treatment with diacetylrhein in comparison with the treatment with naproxen. No noteworthy side effects were observed and also no changes of the clinical laboratory parameters.

4. The action of diacetylrhein was investigated in 23 patients (12/117 with osteoarthrosis in a randomised double blind study using the "double dummy technique" (compatibility study). The dosage administered was 50 mg of diacetylrhein twice daily and 250 mg of naproxen three times daily, The period of treatment was 4 weeks. The test parameters were the oesophagogastroduodenoscopic findings before and after the therapy. Only patients with normal mucosal findings or with slight mucosal lesions (grade 1) were used in the study.

After 4 weeks, the endoscopic findings showed, in one case (10%) in the diacetylrhein group, mucosal lesions of grade 2, whereas, in the naproxen treatment group, 5 patients (50%) showed mucosal lesions of grade 2, 3 and 4. In all cases, a normal take-up finding was present.

Analytical determination of aloe-emodin 50 mg of diacetylrhein are dissolved in 25.3 ml of 0.5M aqueous sodium hydroxide solution in a separating funnel and shaken for 10 minutes. Subsequently, 74.6 ml of a solution are added thereto which contains 0.5M glycine and 0.5M-sodium chloride, a pH value of 9.5 thereby being obtained.

This solution is extracted three times with 25 ml of chloroform. The combined organic phases are extracted once with 10 ml 0.5M of a buffer of pH 9.5 (glycine, sodium hydroxide and sodium chloride) and once with 10 ml 0.01M sulphuric acid. The solvent is removed from the organic phase and the residue is dissolved in 1 ml methanol.

For a standard solution, 2 mg of aloe-emodin are dissolved in 20 ml of N,N-dimethylacetamide and diluted with methanol to a concentration of 2 $\mu g/ml$, corresponding to 40 ppm.

The contents of the solutions is investigated by HPLC. The linearity of the HPLC method was demonstrated with aloe-emodin standard solution in the range of from 0.11 $\mu g/ml$ (corresponding to 2.2 ppm) to 53.6 $\mu g/ml$ (corresponding to 1072 ppm). The content determination takes place with a Merck HPLC column Lichrocart 250-4, packed with LiChrospher-100 RP-18, 5 $\mu m$, at 40° C. with a mobile phase of 1% acetic acid in methanol (v/v), 1% acetic acid in water and acetonitrile in a ratio of 49: 46: 5.

We claim:

1. The method of isolating substantially pure diacetylrhein, which comprises mixing a diacetylrhein containing aloe-emodin composition with an aqueous solution having a pH of 6.5 to 7.5 and a polar organic solvent which is incompletely miscible with said aqueous solution, subjecting the resulting mixture to liquid-liquid partitioning into a light organic phase and a heavy aqueous phase, and recovering substantially pure diacetylrhein from the heavy aqueous phase.

2. The method of preparing diacetylrhein which is substantially free of aloe-emodin components, which comprises:
   a) oxidizing a mixture of rhein-9-anthrone-8-glucoside and aloe-emodin-9-anthrone-8-glucoside to form a mixture of rhein anthraquinone-8-glucoside and aloe-emodin anthra-quinone-8-glucoside,
   b) treating said anthraquinone-8-glucoside mixture with an acid to remove the glucose in the 8-positions and form a mixture of 1,8-dihydroxy-3-carboxy-anthraquinone and 1,8-dihydroxy-3-hydroxymethyl-anthraquinone,
   c) acetylating said mixture of 1,8-dihyroxyanthraquinones to form a mixture of diacetylrhein and 1,8-diacetyl-3-hydroxymethyl-anthraquinone,
   d) mixing said mixture of diacetylrhein and 1,8-diacetyl-3-hydroxymethylanthraquinone with an aqueous solution having a pH of 6.5 to 7.5 and with a polar organic solvent which is incompletely miscible with water,
   e) subjecting the resulting mixture to liquid-liquid partitioning to form a light organic phase and a heavy aqueous phase, and f) recovering substantially pure diacetylrhein from the heavy aqueous phase.

3. The method of claim 2, wherein said oxidizing step is performed with a ferric salt.

4. The method of claim 3, wherein aid oxidizing step is performed with ferric sulfate.

5. The method of claim 1 or 2, wherein said polar organic solvent is butan-2-one.

6. The methods of claim 1 or 2, wherein said aqueous solution is acetate-buffered.

7. The method of claim 1 or 2, wherein the liquid-liquid partitioning step is performed in countercurrent fashion.

8. The method of claim 1 or 2, which further comprises recrystallizing said substantially pure diacetylrhein by
   a) converting it into an alkali metal salt,
   b) dissolving said alkali metal salt in an aqueous alkanol of 1 to 3 carbon atoms, and
   c) precipitating the diacetylrhein by adding an acid to the alkanol solution.

9. The method of claim 1 or 2, which additionally comprises recrystalizing the substantially pure diacetylrhein from ethyl lactate.

* * * * *